(12) United States Patent
Woodside

(10) Patent No.: US 7,316,932 B2
(45) Date of Patent: Jan. 8, 2008

(54) METHOD FOR SEPARATING CELLS

(75) Inventor: Steven M. Woodside, Vancouver (CA)

(73) Assignee: Stemcell Technologies Inc., Vancouver (GB)

( * ) Notice: Subject to any disclaimer, the term of this patent is extended or adjusted under 35 U.S.C. 154(b) by 366 days.

(21) Appl. No.: 10/260,560

(22) Filed: Oct. 1, 2002

(65) Prior Publication Data
US 2003/0124719 A1 Jul. 3, 2003

Related U.S. Application Data

(60) Provisional application No. 60/325,558, filed on Oct. 1, 2001.

(51) Int. Cl.
G01N 1/18 (2006.01)
(52) U.S. Cl. .................... 436/177; 435/7.21; 435/7.23; 435/7.24; 435/803; 436/63; 436/64; 436/518; 436/523; 436/526; 436/527; 436/174; 436/824; 422/72; 422/101
(58) Field of Classification Search .................... 435/2, 435/326, 7.21, 7.23, 7.24, 803; 436/63, 64, 436/514, 518, 520, 523, 526, 527, 174, 824, 436/177; 422/72, 101, 102; 210/781, 782
See application file for complete search history.

(56) References Cited

U.S. PATENT DOCUMENTS

| | | | |
|---|---|---|---|
| 4,004,975 A | 1/1977 | Lionetti et al. | |
| 4,111,199 A | 9/1978 | Djerassi | |
| 4,255,256 A | 3/1981 | Ferrante et al. | |
| 4,927,749 A | 5/1990 | Dorn | |
| 4,927,750 A | 5/1990 | Dorn | |
| 5,397,479 A | 3/1995 | Kass et al. | |
| 5,474,687 A | 12/1995 | Van Vlasselaer | |
| 5,482,829 A | 1/1996 | Kass et al. | |
| 5,489,386 A | 2/1996 | Saunders | |
| 5,576,185 A | 11/1996 | Coulter et al. | |
| 5,646,004 A | 7/1997 | Van Vlasselaer | |
| 5,648,223 A | 7/1997 | Van Vlasselaer | |
| 5,676,849 A | 10/1997 | Sammons et al. | |
| 5,739,033 A | 4/1998 | Soon-Shiong | |
| 5,840,502 A * | 11/1998 | Van Vlasselaer | 435/7.21 |
| 6,004,743 A | 12/1999 | Kenyon et al. | |

OTHER PUBLICATIONS

Patel, D. et al., "Optimization of conditions for specific binding of antibody-coated beads to cells", Journal of Immuloloogical Methods, 1995, pp. 71-80, vol. 184, Elsevier.
Patel, D. et al., "Use of density perturbation to isolate immunology distinct populations of cells", Journal of Immunological Methods, 1993, pp. 241-251, vol. 163, Elsevier.
Bildirici, L. et al., "Fractionation of differentiating cells using density perturbation", Journal of Immunological Methods, 2000, pp. 93-99, vol. 240, Elsevier.
Bildirici, L. et al., "An investigation into the suitability of silica beads for call separations based on density perturbation", Journal of Immunological Methods, 2001, pp. 57-62, vol. 252, Elsevier.
Patel, D. et al, "Separation of T and B lymphocytes from human peripheral blood mononuclear cells using density perturbation methods", Clinica Chimica Acta, 1995, pp. 187-193, vol. 240, Elsevier.
Ellis, W.M. et al, "The Use of Discontinuous Percoll Gradients to Separate Populations of Cells from Human Bone Marrow and Peripheral Blood", Journal of Immunological Methods, 1984, pp. 9-16, vol. 66, Elsevier.
Skoog, W.A. et al., "Studies on the Fibrinogen, Dextran and Phytohemagglutinin Methods of Isolating Leukocytes", Blood, 1956, pp. 436-454, vol. 11.
Ruijs, W.P.M. et al., "Investigation of the Suitability of a New Purification Medium in Comparison with Percoll™ to Separate Bone Marrow", 2000, Ishage, Proceedings, p. 24.
Böyum, A., "Isolation of Leucocytes from Human Blood Further Observations", Scand. J. Clin. Lab. Invest., 1968, pp. 31-50, vol. 21, No. S97.
Böyum, A., "A One-stage Procedure for Isolation of Granulocytes and Lymphocytes from Human Blood", Scand. J. Clin. Lab. Invest., 1968, pp. 51-76, vol. 21, No. S97.
Lillevang, S.T. et al., "A method for isolating granulocytes from rabbit blood without causing activation", Journal of Immunological Methods, 1994, pp. 137-138, vol. 169, Elsevier.
Böyum, A., "Isolation of Leucocytes from Human Blood—A two-phase system for removal of red cells with methylcellulose as erythrocyte-aggregating agent", Scand. J. Clin. Lab. Invest., 1968, pp. 9-29, vol. 21, No. S97.
Fisker, S. et al., "Isolation of rat peritoneal mononuclear and polymorphonuclear leucocytes on discontinuous gradients of Nycodenz", Journal of Immunological Methods, 1990, pp. 31-38, vol. 133, Elsevier.
Ford, T.C. et al., "A new one-step method for the isolation of human mononuclear cells", Journal of Immunological Methods, 1990, pp. 237-241, vol. 134, Elsevier.
Noble, P.B. et al., "Ficoll Floatation for the Separation of Blood Leukocyte Types", Blood, Jan. 1968, pp. 66-73, vol. 31, No. 1.
Ulmer, A.J. et al., "Discontinuous Density Gradient Separation of Human Mononuclear Leucocytes Using Percoll™ as Gradient Medium", Journal of Immunology Methods, 1979, pp. 1-10, vol. 30, Elsevier.
Pertoft, H. et al., The Viability of Cells Grown of Centrifuged in a new Density Gradient Medium, Percoll™, Experimental Cell Research, 1977, pp. 449-457, vol. 110.
Vaughan, W.P., et al., "Breast Cancer Detected in Cell Culture of Histologically Negative Bone Marrow Predicts Systemic Relapse in Patients with Stage I, II, II and Locally Recurrent Disease", Proceedings—Am. Soc. Clin. Oncol—26th Annual Meeting, May 20-22, 1990, p. 9, vol. 9.

(Continued)

Primary Examiner—Gailene Clare R. Gabel
(74) Attorney, Agent, or Firm—Bereskin & Parr; Micheline Gravelle

(57) ABSTRACT

The present invention is related to a method for separating a first population of cells from a second population of cells in a sample by discontinuous density gradient separation using dense particles to target the first population of cells and a density separation medium (DSM) that is at least about 0.001 g/cm³ higher than the density of the second population of cells.

15 Claims, No Drawings

OTHER PUBLICATIONS

Braun, S. et al., "Cytokeratin-Positive Cells in the Bone Marrow and Survival of Patients with Stage I, II, or III Breast Cancer", The New England Journal of Medicine, Feb. 24, 2000, pp. 525-533, vol. 342, No. 8, Massachusetts Medical Society.

Firat, H. et al., "Comparison of CD34+ bone marrow cell purified by immunomagnetic and immunoadsorption cell separation techniques", Bone Marrow Transplantation, 1998, pp. 933-938, vol. 21, Stockton Press.

Thomas, T.E. et al, "Positive Selection of CD34+ Cells from Human Bone Marrow for Indirect Purging of Non-Hodgkin's Lymphoma Cells", Cancer Research, Therapy and Control, 1994, pp. 119-128, vol. 4, No. 2, Harwood Academic Publishers GmbH.

De Wynter, E.A. et al., "Comparison of Purity and Enrichment of CD34+ Cells from Bone Marrow, Umbilical Cord and Peripheral Blood (Primed for Apheresis) Using Five Separation Systems", Stem Cells, 1995, pp. 524-532, vol. 13.

Shpall, E.J. et al., "Transplantation of Enriched CD34-Positive Autologous Marrow Into Breast Cancer Patients Following High-Dose Chemotherapy: Influence of CD34-Positive Peripheral-Blood Progenitors and Growth Factors on Engraftment", Journal of Clinical Oncology, Jan. 1994, pp. 28-36, vol. 12, No. 1.

RosetteSep™ Support Reagents, StemCell Technologies 1999/2000 Catalog Supplement, p. 23A.

* cited by examiner

METHOD FOR SEPARATING CELLS

FIELD OF THE INVENTION

The present invention relates to methods for separating cells. In particular the invention relates to methods for separating cells using dense particles and discontinuous density gradient centrifugation.

BACKGROUND OF THE INVENTION

In many applications it is desirable to enrich, or alternatively deplete, certain cell populations in a biological sample. For example, the separation of specific cell types from peripheral blood, bone marrow, spleen, thymus and fetal liver is key to research in the fields of haematology, immunology and oncology, as well as diagnostics and therapy for certain malignancies and immune disorders.

Most cell separation techniques require that the input sample be a single cell suspension. For this reason, blood has historically been the most common tissue used for cell separations. Purified populations of immune cells such as T cells and antigen presenting cells are necessary for the study of immune function and are used in immunotherapy. Investigation of cellular, molecular and biochemical processes requires analysis of certain cell types in isolation. Numerous techniques have been used to isolate T cell subsets, B cells, basophils, NK cells and dendritic cells from blood for these investigations.

More recently, enzymatic digestion methods have been developed to dissociate tissues from solid organs into single cell suspensions, permitting distinct cell types to be isolated. This is of particular benefit to the study of pluripotent stem cells and tissue-specific stem cells from adults. The rapidly growing field of stem cell research is spurred by the potential of these cells to repair diseased or damaged tissues. Bone marrow (hematopoietic) stem cells were the first adult stem cells to be purified and used clinically and the therapeutic potential of hematopoietic stem cells is now well documented. Transplantation of hematopoietic cells from peripheral blood and/or bone marrow is increasingly used in combination with high-dose chemo- and/or radiotherapy for the treatment of a variety of disorders including malignant, nonmalignant and genetic disorders. Very few cells in such transplants are capable of long-term hematopoietic reconstitution, and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogenic grafts, and tumor cells in autologous transplants that may cause recurrence of the malignant growth. It is also important to debulk the graft by removing unnecessary cells and thus reducing the volume of cyropreservant to be infused.

In certain instances it is desirable to remove or deplete tumor cells from a biological sample, for example in bone marrow transplants. Epithelial cancers of the bronchi, mammary ducts and the gastrointestinal and urogenital tracts represent a major group of solid tumors seen today. Micrometastatic tumor cell migration is thought to be an important prognostic factor for patients with epithelial cancer (Braun et al., 2000; Vaughan et al., 1990). The ability to detect such metastatic cells is limited by the effectiveness of tissue or fluid sampling and the sensitivity of tumor detection methods. A technique to enrich circulating epithelial tumor cells in blood samples would increase the ability to detect metastatic disease and facilitate the study of such rare cells to determine the biological changes which enable spread of the disease.

Hematopoietic cells and immune cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic conceptual approaches to separating cell populations from blood and related cell suspensions using monoclonal antibodies. They differ in whether it is the desired or undesired cells which are distinguished/labeled with the antibody(s).

In positive selection techniques the desired cells are labeled with antibodies and removed from the remaining unlabeled/unwanted cells. In negative selection, the unwanted cells are labeled and removed. Antibody/complement treatment and the use of immunotoxins are negative selection techniques, but FACS sorting and most batch-wise immunoadsorption techniques can be adapted to both positive and negative selection. In immunoadsorption techniques, cells are selected with monoclonal antibodies and preferentially bound to a surface which can be removed from the remainder of the cells e.g. column of beads, flask, magnetic particles. Immunoadsorption techniques have won favour clinically and in research because they maintain the high specificity of cell targeting with monoclonal antibodies, but unlike FACSorting, they can be scaled up to directly process the large numbers of cells in a clinical harvest and they avoid the dangers of using cytotoxic reagents such as immunotoxins and complement. They do however, require the use of a "device" or cell separation surface such as a column of beads, panning flask or magnet.

Current techniques for the isolation of hematopoietic stem cells, immune cells and circulating epithelial tumor cells all involve an initial step to remove red cells prior to antibody mediated adherence to a device or artificial particle (Firat et al., 1988; de Wynter et al., 1975; Shpall et al., 1994; Thomas et al., 1994; Miltenyi Biotec Inc., Gladbach, Germany). In the case of positive selection there is yet another step; removal of the cells from the device or particle. These multiple steps require time and incur cell loss.

Discontinuous density gradient centrifugation is commonly used to isolate peripheral blood mononuclear cells from granulocytes and erythrocytes. FICOLL-PAQUE®, a solution of Ficoll400 and diatrizoate sodium with a density of 1.077 g/ml, (Amersham Pharmacia Biotech AB, Uppsala Sweden) is one of the most popular density separation solutions used for this application. In a Ficoll density separation whole blood is layered over Ficoll, and then centrifuged. The erythrocytes, granulocytes and approximately 50% of the mononuclear cells settle to the cell pellet while the remaining 50% of the mononuclear cells settle to the Ficoll plasma interface. The success of this technique relies on the difference in density between mononuclear cells and granulocytes/erythrocytes as well as the choice of the density separation medium (DSM). During centrifugation, cells that are more dense than the DSM settle through the DSM forming a pellet at the bottom of the tube, while cells that are less dense than the DSM collect at the interface between the DSM and the cell suspension medium (e.g. plasma in the case of peripheral blood, cell culture medium in the case of cultured cells or dissociated tissue cells).

Multiple layers of DSM having different densities can be used to divide the cells into multiple fractions. The same effect can be achieved by centrifuging cells in a medium with a continuous density gradient and then collecting the cells from different positions in the gradient. Sedimentation rate can also be used to separate cells of different density, but the separation time is Influenced not only by density but also the viscosity of the suspension and the cell size.

All density separation techniques have the same basic limitation; they can not separate subpopulations of cells with overlapping density distributions such as human lymphocyte subsets. Simple density separation techniques do not offer the high cell specificity offered by antibody-mediated techniques. To address this, dense particles have been targeted to cells using monoclonal antibodies with affinity to cells surface antigens and used in discontinuous or continuous density gradient centrifugation to separate cell populations with similar densities (Bildirici and Rickwood, 2001; Bildirici and Rickwood, 2000; Patel and Rickwood, 1995; Patel et al. 1993; U.S. Pat. No. 5,840,502; and StemCell Technologies, Supplement to 1999/2000 Catalogue). There are two advantages of using a discontinuous density gradient rather than a continuous density gradient in dense particle mediated cell separation. Discontinuous gradients are easier to prepare and offer a visible boundary (interface) where cells not bound to particles selectively collect.

Several patents (U.S. Pat. No. 5,840,502, U.S. Pat. No. 5,648,223, U.S. Pat. No. 5,646,004 and U.S. Pat. No. 5,474,687) describe the use of dense particles for negative selection by selectively targeting and pelleting undesired cell types using discontinuous density gradient separations. These patents state that the optimum density of the DSM for dense particle separation is within ±0.0005 to ±0.0002 g/cm$^3$ of the density of the desired cell population.

There are no documented techniques for positive selection of cells using dense particles and discontinuous density gradients. In positive selection the desired cells are targeted with antibodies and dense particles and pelleted during separation.

SUMMARY OF THE INVENTION

The invention relates to the use of dense particles and discontinuous density gradients to separate populations of cells from a mixed cell suspension. It has been found that the use of dense particles to target a first population of cells and a density separation medium (DSM) with a density at least 0.001 g/cm$^3$ higher than the density of a second population of cells not targeted by the dense particles, offers more effective cell separation through increased recovery of the non-targeted population of cells at the interface between the DSM and the sample suspension without affecting the pelleting of the targeted cells. This is contrary to current practice and the teachings of U.S. Pat. Nos. 5,840,502, U.S. Pat. No. 5,648,223, U.S. Pat. No. 5,646,004 and U.S. Pat. No. 5,474,687, which teach that the DSM should have a density preferably within ±0.0005 g/cm$^3$ and more preferably within ±0.0002 g/cm$^3$ of the desired cell density. In these patents, the desired cells are not targeted by the dense particles.

Accordingly, the present invention provides a method for separating a first population of cells from a second population of cells in a sample comprising:

linking dense particles to the first population of cells in the sample;

layering the sample over a density separation medium (DSM) having a density at least about 0.001 g/cm$^3$ greater than the mean density of the second population of cells; and allowing the cells to settle, wherein the particle-linked first population of cells will settle to below the interface between the DSM and the sample and the second population of cells will settle to the interface between the DSM and the sample.

In the method of the invention, the first population of cells (i.e. those linked to the dense particles) will settle out below the interface between the DSM and the sample and the second population of cells will settle at the interface between the DSM and the sample. Each population of cells may be thus isolated or recovered.

The method of the invention may be used to positively or negatively select a population of desired cells. For negative selection, the desired cells will be the second populations of cells and are accordingly recovered from the interface between the DSM and the sample. For positive selection, the desired cells will be the first population of cells, which are linked to the dense particles, and thus are recovered from the area below the interface between the DSM and the sample. When positive selection techniques are used, it is typically desired to remove the dense particles from the desired cells using enzymatic, chemical or physical means.

In embodiments of the invention, the settling of the cells is accelerated by centrifugation.

The invention includes all uses of the above-described methods as well as kits to perform the methods of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION (i) Methods of the Invention

As hereinbefore stated, it has been found that the use of dense particles to target a first population of cells and a density separation medium (DSM) with a density at least 0.001 g/cm$^3$ higher than the mean density of the a second population of cells not targeted by the dense particles, offers more effective cell separation than separations according to current practice.

Accordingly, the present invention relates to a method for separating a first population of cells from a second population of cells in a sample comprising:

linking dense particles to the first population of cells in the sample;

layering the sample over a density separation medium (DSM) having a density at least about 0.001 g/cm$^3$ greater than the mean density of the second population of cells; and allowing the cells to settle, wherein the particle-linked first population of cells will settle to below the interface between the DSM and the sample and the second population of cells will settle to the interface between the DSM and the sample.

As used herein, the "first population of cells" (i.e. those linked to the dense particles) are the cells which settle out below the interface between the DSM and the sample and the "second population of cells" are those cells which settle at the interface between the DSM and the sample. As used herein, the term "below the interface between the DSM and the sample" typically means in a pellet at the bottom of the container. Due to this difference in location, each population of cells may be isolated or recovered. Accordingly, the present invention further comprises the step of isolating the first population of cells from below the interface between the DSM and the sample and/or isolating the second population of cells from the interface between the DSM and the sample. When the density of the DSM is at least about 0.001 g/cm$^3$ greater than the mean density of the second population of cells, more effective cell separations are achieved compared to separations using currently practiced methods.

As used herein, the term "below the interface between the DSM and the sample" typically means in a pellet at the bottom of the container.

The term "desired cells" as used herein refers to a population of cells that one wishes to isolate from a sample. The population of desired cells may contain one or more cells types.

The term "undesired cells" as used herein refers to a population of cells that one wishes to remove from a sample. The population of undesired cells may contain one or more cell types.

In embodiments of the invention, the cells are settled using gravity or centrifugation. In preferred embodiments, the settling of the cells is accelerated using centrifugation.

When the desired cells are the second population of cells, a negative selection protocol is employed. In this instance, the dense particles are targeted to the first population of cells, i.e. undesired cells, which settle to an area below the interface between the DSM and the sample. When centrifugation is employed to accelerate settling, the first population of cells will settle more quickly to the bottom of the sample container to form a pellet. The second population of cells, or desired cells, may be recovered from the interface between the DSM and the sample. Accordingly, the method of the present invention further comprises the step of recovering the second population of cells from the interface between the DSM and the sample.

When the desired cells are the first population of cells, a positive selection protocol is employed. In this instance, the dense particles are targeted to the desired cells, which settle to an area below the interface between the DSM and the sample. When centrifugation is employed to accelerate settling, the desired cells will settle more quickly to the bottom of the container to form a pellet. When positive selection is employed, it is desirable to remove the dense particles from the cells. Accordingly, the method of the present invention further comprises the step of recovering the first population of cells from an area below the interface between the DSM and the sample and, optionally, removing the dense particles from the first population of cells. Removal of the dense particles from the first population of cells may be carried out using enzymatic, chemical or physical methods well known in the art. For example, using proteolytic enzymes such, as papain.

In a preferred embodiment of the invention, the first population of cells is the undesired cells and the second population of cells are the desired cell, or a negative selection protocol is used to separate desired cells from undesired cells.

The sample can be any cell suspension from which one wishes to separate desired cells. As such, the sample will generally contain a mixture of desired cells and undesired cells suspended typically as single cells in a liquid medium. The sample can be obtained from both in vivo and in vitro sources. Examples of sources include, but are not limited to, peripheral blood, bone marrow, spleen, thymus and fetal liver. Specific cell types that may be isolated using the method of the invention include, but are not limited to, T cells, B cells, basophils, NK cells, dendritic cells, monocytes, macrophages, megakaryocytes, platelets, eosinophils, neutrophils, hematopoietic stem cells, mesenchymal stem cells, endothelial cells, epithelial cells, fibroblasts and tumour cells.

A variety of commercially available materials may be used as the DSM in the method of the invention, including, but not limited to FICOLL-PAQUE®; LYMPHOPREP®, a solution containing diatrizoate (9.1% w/v) and polysaccharide (5.7% w/v); any sugar solution, e.g. sucrose; dextran; any protein solution, e.g. bovine serum albumin (BSA); iodinated low molecular weight compounds such as Metrizamide and heavy salts, e.g. cesium chloride. In an embodiment of the invention, the density separation medium (DSM) is prepared by mixing hetastarch, iodixanol and water in different proportions such that the desired density and osmolarity is obtained.

The density of the DSM should be at least about 0.001 g/cm$^3$, preferably about 0.002 g/cm$^3$, more preferably about 0.004 g/cm$^3$, higher, than the mean density of the density of the second population of cells (i.e. the cells that are not targeted by the dense particles). As used herein, the term "mean density of the second population of cells" refers to the density of the second population of cells as determined using density gradient centrifugation with a series of DSM having different densities and without dense particles (for example, see Example 6 herein).

Mammalian cells and cells from most multi-cellular organisms have semi-permeable membranes and are therefore sensitive to changes in the osmolarity of their environment. Cell density will increase with increasing osmolarity of the surrounding solution. The mean density of some human blood cell types is given in Table 1 for solutions iso-osmolar to plasma (270-290 mOsm) and for solutions hyper-osmolar to plasma (300-310 mOsm). This table shows that the density of the cells is strongly dependent on solution osmolarity. Thus mean cell density of a given population is defined in the context of the solution osmolarity. In discontinuous density gradient separation, the mean cell density of a given population of cells is said to be equal to the density of the DSM if the number of cells in the given population recovered at the interface is approximately the same as the number recovered in the pellet (or if 50% of the initially present second population of cells are recovered at the interface when recovery in the pellet cannot be reliably determined).

The osmolarity of the DSM is preferably approximately the same as the osmolarity of the sample (i.e the DSM is approximately iso-molar to the sample). The term "approximately the same" means that the osmolarity of the DSM is in the range of about plus or minus 10% of the osmolarity of the sample. Most preferably, the osmolarity of the DSM is in the range of about 270 to about 300 mOsm.

The density of the DSM should also be lower than the effective density of the first population of cells when linked to dense particles such that most of the particle-linked first population of cells settle to the pellet during density gradient separation.

The effective density of the particle-bound cells will depend on the size and density of the cells and the size, density and number of particles linked to the cells. For any cell linked to dense particles, the effective density can be defined as the product of the cell volume ($V_c$) and cell density ($\rho_c$), plus the product of the total volume of the particles ($V_p$) linked to the cell and the density of the particles ($\rho_p$), all divided by the total volume of the cell and the particles linked to the cell:

$$\frac{V_c \rho_c + V_p \rho_p}{V_c + V_p}$$

For example, a cell with a diameter of 10 μm and a density of 1.0 g/cm³ linked to one particle with a diameter of 10 μm and a density of 2.0 g/cm³ would have an effective density of 1.5 g/cm³. The same cell linked to 9 particles with a diameter of 10 μm and a density of 2.0 g/cm³ would have an effective density of 1.9 g/cm³.

The methods of the invention may be carried out in any suitable container, for example a centrifuge tube or syringe.

The method of the invention can be used to separate cells into multiple fractions by using multiple layers of DSM each having a density that is at least about 0.001 g/cm³ greater than the mean density of the population of cells that one wishes to have settle at the interface between that DSM and the sample. Accordingly, in a further embodiment of the present invention there is provided a use, for discontinuous density gradient separation of one or more populations of cells from a sample, of a DSM having a density that is at least about 0.001 g/cm³ greater than the mean density of the population of cells that is to settle at an interface between the DSM and the sample.

The use of particles to adjust the density of the undesired or desired cells during density gradient cell separations is described in U.S. Pat. No. 5,840,502, the contents of which are incorporated herein by reference.

In embodiments of the present invention, the first population of cells may be linked to dense particles through various types of binding including, but not limited to, drug-drug receptor, antibody-antigen, hormone-hormone receptor, growth factor-growth factor receptor, carbohydrate-lectin, nucleic acid sequence-complementary nucleic acid sequence, enzyme-cofactor or enzyme-inhibitor binding. Preferably, the cells to be linked to the dense particles are defined by specific surface proteins and the dense particles are linked to these cells by antibodies specific for the cell surface proteins.

In one embodiment of the invention, the antibodies specific for cell surface proteins on the cells to be linked to the dense particles are in an antibody composition or cocktail. Examples of antibody compositions or cocktails which may be used to target a range of cell types are described U.S. Pat. No. 6,448,075, the contents of which are incorporated herein by reference. Examples of antibody compositions or cocktails which may be used to target hematopoietic stem cells and progenitor cells are described in U.S. Pat. Nos. 5,877,299, 6,117,985 and 6,307,575, the contents of which are incorporated herein by reference.

In further embodiments of the present invention, the dense particles serve to increase the effective density of the first population of cells and may be, for example, selected from the group consisting of red blood cells, silica particles, metal particles, metal oxide particles, polymer particles, glass particles. Red blood cells may be linked to the first population of cells using tetrameric antibody complexes as described in Example 2 herein. Other particles may be linked to the first population of cells by coating the particles with, for example, antibodies or dextran.

Kits

Density separation media, cell specific targeting agents and/or dense particles for the separation of specific cell types may be prepared and packaged in convenient kits, packaged into suitable containers. Accordingly, the present invention relates to a kit for separating a first population of cells from a second population of cells in a sample comprising one or more aliquots of a density separation medium having a density at least about 0.001 g/cm³ higher than the mean density of the second population of cells, one or more aliquots of cell-specific targeting agents to target dense particles to the first population of cells and one or more aliquots of dense particles.

In an embodiment of the invention, applications that use red blood cells as dense particles to separate a first population of cells from a second population of cells from whole peripheral blood, as in Examples 2 and 3, the cell specific targeting reagents may include one or more aliquots of tetrameric antibody complex cocktails that link the first population of cells to the red blood cells.

In a further embodiment of the invention, a kit for separating a first population of cells from a second population of cells in a sample consisting more generally of nucleated cells, may comprise one or more aliquots of a density separation medium having a density at least about 0.001 g/cm³ higher than the mean density of the second population of cells, and one or more aliquots of cell targeting reagents. In embodiments of the invention the cell targeting reagents are selected from dense particles coated with one or more cell-specific binding agents that target the first population of cells, for example, antibody coated dense particles that target the first population of cells, or one or more aliquots of a cell-targeting reagent, for example an antibody or antibody cocktail, that binds to the first population of cells and one or more aliquots of dense particles that then bind to those cells through interactions with the cell targeting reagent. In specific embodiments of the invention, the cell-targeting reagents are tetrameric antibody complexes.

With particular regard to density separation media packaged in "kit" form, it is preferred that aliquots of the media be packaged in separate containers, with each container including a sufficient quantity of reagent for at least one assay to be conducted. A preferred kit is typically provided as an enclosure (package) comprising one or more containers for the within-described reagents.

Printed instructions providing guidance in the use of the packaged reagent(s) may also be included, in various preferred embodiments. The term "instructions" or "instructions for use" typically includes a tangible expression describing the reagent concentration or at least one assay method parameter, such as the relative amounts of reagent and sample to be mixed, maintenance time periods for reagent/sample mixtures, temperature, buffer conditions, and the like.

The following non-limiting examples are illustrative of the present invention:

EXAMPLES

Example 1

Preparation of Density Separation Media (DSM)

Density separation media (DSM) were prepared at different densities by mixing hetastarch, iodixanol and water in different proportions such that the desired density was obtained and the osmolarity was between 270 and 300 mOsm. The hetastarch and odixanol components of this DSM serve the same function as the polysaccharide and metrizoate components respectively in both FICOLL-PAQUE® and LYMPHOPREP®.

Example 2

Method to Negatively Select Cells from Whole Human Peripheral Blood Using the Method of the Invention With Red Blood Cells as Dense Particles Preparation of Tetramers In order to prepare a tetrameric antibody complex for use in the method of the present invention, the following protocol may be used: (a) take 1 mg of antibody specific for cells to be bound for red blood cells (e.g. anti-CD2, CD3, CD4, CD8, CD14, CD16, CD19 etc.); (b) add 3 mg anti-Glycophorin A antibody (against red blood cells); mix well (c) then add 4.0 mg of P9 antibody or 2.72 mg of the P9 F(ab')$_2$ antibody fragment. Incubate overnight at 37° C. The P9 antibody binds the Fc portion of the antibodies added in steps (a) and (b) resulting in a tetrameric antibody complex. For more information on the preparation of tetramers see U.S. Pat. No. 4,868,109 to Lansdorp, which is incorporated herein by reference. Tetrameric antibody complexes incorporating different antibodies to antigens expressed on nucleated cells are prepared separately and then mixed.

The antibody compositions are made by combining various tetrameric antibody complexes depending on which cells one wishes to pellet during density gradient separation. The concentration of the various tetrameric antibody complexes varies: typically antibodies to antigens expressed on nucleated cells are at 10-30 µg/mL in tetrameric complexes. The composition is then diluted ¹⁄₁₀ into the cells so the final concentrations of each anti nucleated cell antibody in the cell suspensions is 1.0-3.0 µg/mL.

Separation Method

A negative selection protocol for separating cells from whole peripheral blood is set out below.
1. Add 100 µL antibody composition per mL of whole peripheral blood.
2. Incubate 20 minutes at room temperature.
3. Dilute sample with an equal volume of phosphate buffered saline (PBS)+2% fetal calf serum (FCS) and mix gently.
4. Layer the diluted sample on top of the DSM.
5. Centrifuge for 20 minutes at 1200×g, room temperature, with the brake off.
6. Remove the desired cells from the DSM:plasma interface.
7. Wash desired cells with 5-10×volume of PBS+2% FCS.

Example 3

Method to Positively Select Cells from Whole Human Peripheral Blood Using the Method of the Invention With Red Blood Cells as Dense Particles Preparation of Tetramers Tetrameric antibody complexes were prepared as described in Example 2. The antibody compositions are one or more types of tetrameric antibody complexes depending on which cells one wishes to select.

Separation Method

A positive selection protocol for separating cells from peripheral blood is set out below.
1. Add 100 µL antibody composition per mL of peripheral blood.
2. Incubate 20 minutes at room temperature.
3. Dilute sample with an equal volume of phosphate buffered saline (PBS)+2% fetal calf serum (FCS) and mix gently.
4. Layer the diluted sample on top of the DSM.
5. Centrifuge for 20 minutes at 1200×g, room temperature, with the brake off.
6. Remove the desired cells from the pellet.
7. Wash desired cells with 5-10×volume of PBS+2% FCS.
8. Lyse red blood cells by adding 10× volume of lysis buffer such as ammonium chloride, incubate 5-10 min, spin down and resuspend in PBS+2% FCS

Example 4

Method to Negatively Select Cells from Human Peripheral Blood Mononuclear Cell Suspensions Using the Method of the Invention With Silica Particles as Dense Particles Preparation of Tetramers In order to prepare a tetrameric antibody complex for use in the method of the present invention, the protocol describe in Example 2 may be used with the following changes: (a) take 1 mg of antibody specific for cells to be pelleted (e.g. anti-CD2, CD3, CD4, CD8, CD14, CD16, CD19 etc.); (b) add 2 mg anti-Dextran antibody; mix well (c) then add 3.0 mg of P9 antibody or 2.04 mg of the P9 F(ab')$_2$ antibody fragment.

The antibody compositions are made by combining various tetrameric antibody complexes depending on which cells one-wishes to pellet during density gradient separation.

Preparation of Mononuclear Cell Suspension

Previously frozen mononuclear cells obtained by FICOLL-PAQUE® density gradient separation were thawed and washed once with a 10×volume of PBS+ 2% FCS. The cells were resuspended at 5×10$^7$ cells/mL.

A negative selection protocol for density gradient separation from human peripheral blood mononuclear cells using silica particles is set out below. The silica particles were coated with dextran.
1. Add dextran-coated silica particles to cell suspension and mix.
2. Add 100 µL antibody composition per mL of cell suspension and mix.
3. Incubate 20 minutes at room temperature.
4. Dilute sample with an equal volume of phosphate buffered saline (PBS)+2% fetal calf serum (FCS) and mix gently.
5. Layer the diluted sample on top of the DSM.

6. Centrifuge for 20 minutes at 1200×g, room temperature, with the brake off.
7. Remove the desired cells from the DSM: buffered saline interface
8. Wash desired cells with 5-10×volume of PBS+2% FCS.

Example 5

Method to Negatively Select Cells from Mouse Spleen Cell or Bone Marrow Cell Suspensions Using the Method of the Invention With Silica Particles as Dense Particles A protocol for negative selection of cells from mouse spleen or bone marrow is set out below.
1. Obtain single cell suspensions from murine spleen or bone marrow using standard procedures
2. Add rat anti-mouse antibodies that bind to specific cell surface proteins on unwanted cells at a final concentration of between 1.0 and 3.0 μg/mL. For example to enrich for murine CD4+cells, add antibodies targeting CD11b, CD45R, CD8, erythroid cells (TER119) and myeloid differentiation antigen (Gr-1).
3. Incubate for at least 5 min
4. Wash cells then incubate with silica particles that are coated with goat-anti-mouse antibodies.
5. Layer the cell-particle mixture over DSM
6. Centrifuge for 20 min at 1200×g with no brake
7. Remove desired cells from the DSM: buffered saline interface.
8. Wash desired cells with 5-10×volume of PBS+2% FCS.

Example 6

Determination of Cell Densities

Three (3) mL of various DSM were aliquoted in separate 15 mL conical polypropylene tubes. The DSM and their respective density and osmolarity were FICOLL-PAQUE® Plus from Pharmacia (1.077, g/cm$^3$, 300-310 mOsm) and three density separation media (DSM) prepared as described in Example 1 with densities of 1.077, 1.081 and 1.085 g/cm$^3$ and Osm=290 mOsm. Single cell suspensions were obtained from mouse spleens using standard procedures. A total of 2×10$^7$ cells was diluted in 2 ml of the appropriate buffer. The diluted cell suspensions were layered on top of each of the DSM. The samples were centrifuged in a swinging bucket centrifuge at 1200×g for 10 minutes at room temperature with the centrifuge brake off. The original spleen cell suspension, light density cells (collected from the buffer: DSM interface) and pellet cells were analyzed by flow cytometry.

The results in Table 2 show that the recovery of lymphocytes and granulocytes increases with increasing density of the DSM up to 1.085 g/cm$^3$. The recovery with FICQLL-PAQUE® is lower than with the DSM prepared with the same density likely because it has a lower osmolarity than FICQIL-PAQUE® (see Table 1). A DSM density of 1.081 g/cm$^3$ is ideal for depleting RBC while maintaining a high lymphocyte recovery according to these data. The data in Table 2 also show that the average lymphocyte and granulocyte density is between 1.077 and 1.081 g/cm$^3$. According to the prior art a OSM with a density in this range is preferred for dense particle assisted density separations. Further examples will show that the preferred DSM density is higher than the average lymphocyte or granulocyte density. Although the data in Table 2 relate specifically to mouse spleen cells, this type of analysis can be applied to any cell population to determine the recovery and purity as a function of DSM density.

Example 7

Effect of DSM Density on the Negative Selection of Murine Spleen and Bone Marrow Cells Using Silica Particles and Discontinuous Density Gradient Separation CD4$^+$ cells were enriched from murine spleen suspensions following the method of Example 5 using a cocktail of antibodies targeting CD11b, CD45R, CD8, erythroid cells (TER119) and myeloid differentiation antigen (Gr-1). CD8$^+$ cells were similarly enriched using a cocktail of antibodies targeting CD11b, CD45R, CD4, erythroid cells (TER119) and myeloid differentiation antigen. Murine progenitors, defined as Sca1$^+$/lineage negative (CD3, CD11b, CD45R and Gr-1 negative), were enriched from murine bone marrow using a cocktail of antibodies targeting CD5, CD11b, CD45R, erythroid cells (using TER antibody), myeloid differentiation antigen (Gr-1) and neutrophils (using 7-4 antibody).

The results in Table 3 show that recovery of the desired cells increases with increasing density of the DSM and that the range of useful densities is well above 1.081 g/cm$^3$ which was shown in Example 6 to be the upper limit of the density of the desired lymphocytes. Thus, it is advantageous to use a DSM with a higher density than the density of the desired cell for murine cell separations.

Example 8

Effect of DSM Density on Negative Selection of Human Peripheral Blood Cells Using Red Blood Cells as Dense Particles and Discontinuous Density Gradient Separation Human peripheral blood cells were separated using the method described in Example 2. The T (CD3+) cell enrichment cocktail included antibody complexes targeting CD16, CD19, CD36 and CD56. The CD4+ T cell enrichment cocktail included antibody complexes targeting CD8, CD16, CD19, CD36 and CD56. The CD8+ T cell enrichment cocktail included antibody complexes targeting CD4, CD16, CD19, CD36 and CD56. The B (CD19+) cell enrichment cocktail included antibody complexes targeting CD2, CD3, CD16, CD36 and CD56. The NK (CD56+) cell enrichment cocktail included antibody complexes targeting CD3, CD4, CD19, CD36 and CD66b.

Table 4 shows data obtained from two different samples, where one sample was incubated with a cocktail of antibody complexes to enrich T-cells and the other was incubated with the B-cell enrichment cocktail. The samples were then layered in 3 equal volume aliquots over each of FICOLL-PAOUE®(1.077 g/cm$^3$, 300-310 mOsm) and two DSM prepared with densities of 1.081 and 1.085 g/cm$^3$ (290 mOsm) and separated following Example 1. The tabulated values are the average of the results for the n=3 separations for each DSM. The results in Table 4 clearly show that the recovery of the desired cells is improved with increased DSM density and that the purity of the desired cell population obtained is not adversely affected up to a density of 1.085 g/cm$^9$.

The results summarized in Table 5 are from the separation of 3 samples where such sample was divided into 5 equal parts and incubated with a cocktail of antibody complexes for the enrichment of the 5 desired cell types listed following the method of Example 2. Each ot these volumes was then diluted, split into two equal volumes and layered over either FICOLL-PAQUE® (1.077 g/cm³, 300-310 mOsm) or a DSM prepared with a density of 1.081 g/cm³ (290 mOsm). Table 5 shows that the recovery of desired cells is higher using a DSM with a higher density than FICOLL-PAQUE® despite the difference in osmolarity. The purity of the desired population is equivalent or higher using DSM. The optimum DSM density for the isolation of T, B and NK cells from whole blood in conjunction with dense particle enrichment is thus higher than that of FICOLL-PAQUE® which is close to the density of MNC at 300-310 mOsm (see Table 1) and is optimum for MNC isolation in the absence of dense particle enrichment. This example shows that the preferred DSM density for density separations of human lymphocyte subsets using red blood cells as dense particles to deplete unwanted cells is substantially higher than the density of the desired lymphocytes.

Example 9

Depletion of Undesired Human Peripheral Blood Cells Using Dextran Coated Silica Particles and Discontinuous Density Gradient Separation Previously frozen mononuclear cells were incubated with anti-CD3: anti-dextran bi-specific antibody complex (as described in Example 4) at 1.0 µg/mL anti-CD03 antibody for 20 min at room temperature, then washed to remove excess tetramer. Dextran coated silica particles were then added at 2.5 µg/mL, incubated for 20 minutes at room temperature and then diluted 4 fold and layered over either FICOLL-PAQUE® (1.077 g/cm³, 300-310 mOsm) or a DSM with a density of 1.081 g/cm³ (290 mOsm) in a centrifuge tube. The tubes were centrifuged for 20 min at 1200×g with no brake and the cells at the interface were recovered and washed 1×. The CD3+ cell log depletion was determined by taking the log of the number of cells labeled with sheep anti-mouse (SAM)-FITC+ in the start sample divided by the number in the final sample. SAM antibodies bind to cells that have been targeted by murine antibodies including the anti-CD3: anti-dextran bi-specific antibodies.

Table 6 shows that the log depletion of CD3+ cells was equivalent for both DSM but that the recovery of CD3-negative cells was higher using DSM (1.081 g/cm³, 290 mOsm) because more cells were buoyant than in FICOLL-PAQUE®. The density of FICOLL-PAQUE® is close to the mean lymphocyte density (see Table 1). This example shows that the preferred density of the DSM for density separations using silica particles to deplete unwanted cells is higher than the lymphocyte density to provide improved recovery of CD3-negative cells without affecting CD3+ cell depletion efficiency.

Example 10

Effect of DSM Density on Positive Selection of CD3+ Human Peripheral Blood Cells Using Red Blood Cells as Dense Particles and Discontinuous Density Gradient Separation Three DSM were prepared following Example 1 with densities of 1.081, 1.085 and 1.090 g/cm³. Anti-CD3: αGlyA antibody complexes were prepared as described in Example 2. Following the positive selection separation method described in Example 5, four equal volume aliquots of blood were incubated with the anti-CD3: αGlyA antibody complexes and layered over each of FICOLL-PAQUE® (1.077 g/cm³, 300-310 mOsm) and the three DSM with densities of 1.081, 1.085 and 1.090 g/cm³ (290 mOsm) and separated by centrifugation. The desired cells were recovered from the pellet and the red blood cells were removed from the desired cells by lysis using an ammonium chloride solution.

The results in Table 7 clearly show that the purity of the desired cells is improved using a DSM with a density of 1.081 g/cm³ instead of FICOLL-PAQUE® (1.077 g/cm³, 300-310 mOsm). The undesired dense cells, such as granulocytes, are more buoyant in the higher density DSM and do not settle to the pellet. The recovery of desired cells generally decreases with increasing DSM density. This is due to the greater buoyancy at the desired cells in DSM of increasing density and the greater number of linked RBC necessary to change the effective density of the cells such that they will pellet. This example shows that the preferred DSM density for positive selection density separations of human CD3+ cells using red blood cells as dense particles is substantially higher than the density of FICOLL-PAQUE® despite the difference in osmolarity and is higher than the density of the undesired cells.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Mean density of human peripheral blood cells in solutions iso-osmolar to plasma and hyper-osmolar to plasma

| | Cell Density (g/cm³) in: | |
|---|---|---|
| Cell Type | Iso-osmolar solution (270-290 mOsm) | Hyper-osmolar solution (300-310 mOsm)$ |
| Monocytes | 1.064* | NA |
| Lymphocytes | 1.072* | 1.077$ |
| Neutrophils | 1.078* | NA |

NA: not available
*Nycomed Amersham "Centrifugation Techniques"
$FICOLL-PAQUE ® Product information sheet

TABLE 2

Recovery of red blood cells (RBC), lymphocytes (Lymphs) and granulocyte (Grans) populations in the interface and pellet after density gradient centrifugation of murine spleen cells over density media of various densities

| | Interface | | | Pellet | | |
|---|---|---|---|---|---|---|
| DSM Density (g/cm³) | RBC % recovery | Lymphs % recovery | Grans % recovery | RBC % recovery | Lymphs % recovery | Granus % recovery |
| 1.077* | 0.2 | 20 | 18 | 76 | 20 | 79 |
| 1.077$ | 0.2 | 48 | 50 | 92 | 50 | 42 |

TABLE 2-continued

Recovery of red blood cells (RBC), lymphocytes (Lymphs)
and granulocyte (Grans) populations in the interface and pellet after
density gradient centrifugation of murine spleen cells over density
media of various densities

| DSM Density (g/cm³) | Interface | | | Pellet | | |
|---|---|---|---|---|---|---|
| | RBC % recovery | Lymphs % recovery | Grans % recovery | RBC % recovery | Lymphs % recovery | Granus % recovery |
| 1.081$ | 0.3 | 68 | 38 | >100 | 1.4 | 2 |
| 1.085$ | 16 | 86 | 80 | 69 | 1 | 1.13 |
| 1.077* | <0.1 | 5.3 | 10.4 | >100 | 83 | 96 |
| 1.077$ | 0.2 | 15 | 16 | >100 | 76 | 67 |
| 1.081$ | 0.3 | 101 | >100 | >100 | 5.9 | 12 |
| 1.085$ | 3.6 | >100 | >100 | 25 | 1.9 | 3.2 |

*FICOLL-PAQUE ®: 300–310 mOsm
$Other DSM: 290 mOsm

TABLE 3

Purity and recovery of negatively selected murine cells using
GAR-coated silica particles and discontinuous density gradient
separation with DSM of different densities (290 mOsm).

| Cell type enriched | DSM Density (g/cm³) | % Purity in Start | % Purity in Enriched | % Recovery in Enriched |
|---|---|---|---|---|
| CD8+ cells | 1.0950 | 9.4 | 88, 86 | 49, 49 |
| (n = 2) | 1.0900 | 9.4 | 90, 90 | 32, 29 |
| Sca+, lin− | 1.0900 | 1.6 | 10, 11 | 52, 39 |
| (n = 2) | 1.0875 | 1.6 | 9.2, 9.4 | 47, 41 |
| | 1.0800 | 1.6 | 8.6, 8.5 | 33, 37 |
| CD4+ cells | 1.0900 | 21 | 84, 81 | 34, 27 |
| (n = 2) | 1.0875 | 21 | 88, 86 | 34, 34 |
| | 1.0800 | 21 | 84, 84 | 29, 30 |
| CD4+ cells | 1.0950 | 24 | 87 | 26 |
| (n = 1) | 1.0900 | 24 | 89 | 23 |

TABLE 4

Purity and recovery of human cells negatively selected from
whole blood using red blood cells as dense particles and discontinuous
density gradient separation with DSM of different densities.

| DSM Density (g/cm³) | % purity desired cells | % recovery desired cell |
|---|---|---|
| T cell (CD3+) enrichment | | |
| 1.077 (FICOLL-PAQUE ®)* | 96 | 26 |
| 1.081$ | 96 | 44 |
| 1.085$ | 96 | 55 |
| B cell (CD19+) enrichment | | |
| 1.077 (FICOLL-PAQUE ®)* | 86 | 62 |
| 1.081$ | 88 | 96 |
| 1.085$ | 85 | 91 |

*FICOLL-PAQUE ®: 300-310 mOsm
$Other DSM: 290 mOsm

TABLE 5

Purity and recovery of human cells negatively selected from
whole blood using red blood cells as dense particles and
discontinuous density gradient separation with FICOLL-PAQUE ® (1.077
g/cm³, 300-310 mOsm) and DSM at 1.081 g/cm³ (290 mOsm).

| | Purity | | Recovery | |
|---|---|---|---|---|
| Desired Cell Population | FICOLL-PAQUE ® | DSM (1.081 g/cm³) | FICOLL-PAQUE ® | DSM (1.081 g/cm³) |
| T cell (CD3+) | 98% | 98% | 61% | 71% |
| CD4+ T cell | 94% | 94% | 67% | 78% |
| CD8+ T cell | 85% | 85% | 42% | 43% |
| B cell (CD19+) | 84% | 90% | 72% | 87% |
| NK cell (CD56+) | 82% | 85% | 24% | 27% |

TABLE 6

Depletion of human CD3 positive T cells and recovery of CD3
negative cells using silica particles and discontinuous density gradient
separation with FICOLL-PAQUE ® (1.077 g/cm³, 300-310 mOsm)
and DSM at 1.081 g/cm³ (290 mOsm).

| DSM | % CD3+ in start sample | % CD3+ in depleted sample | Log depletion CD3+ | % Recovery CD3− cells |
|---|---|---|---|---|
| DSM 1.081 g/cm³ | 39 | 4.3 | 1.6 | 34 |
| FICOLL-PAQUE ® | 39 | 9.9 | 1.4 | 26 |
| DSM 1.081 g/cm³ | 39 | 4.0 | 1.7 | 41 |
| FICOLL-PAQUE ® | 39 | 3.7 | 1.8 | 31 |

TABLE 7

Purity and recovery of human CD3+ cells positively selected
from human blood using red blood cells as dense particles and
discontinuous density gradient separation.

| DSM density (g/cm³) | % Purity | % Recovery |
|---|---|---|
| 1.077 (FICOLL-PAQUE ®)* | 80.2 | 42 |
| 1.081$ | 93.6 | 51 |
| 1.085$ | 89.0 | 43 |
| 1.090$ | 83.9 | 41 |

*FICOLL-PAQUE ®: 300-310 mOsm
$Other DSM: 290 mOsm

Full Citations for References Referred to in the Specification

1. Braun et al., N. Engl. J. Med., 342:525:533.
2. deWynter, E. A. et al., 1975, Stem Cells, Vol. 13:524-532.
3. Firat et al., 1988, Bone Marrow Transplantation, Vol. 21:933-938.
4. Shpall, E. J., et al. 1994, J. of Clinical Oncology 12:28-36.
5. Thomas, T. E., 1994, Cancer Research, Therapy and Control 4(2): 119-128.
6. Vaughan et al., 1990, Proc. Am. Soc. Clin. Oncol. 9:9.
7. Patel et al., 1995, Clinica Chimica Acta 240: 187-193.
8. Patel and Rickwood, 1995, J. Immunol. Meth. 184: 71-80.
9. Bildirici and Rickwood, 2000, J. Immunol. Meth. 240: 93-99.
10. Bildirici and Rickwood, 2001, J. Immunol. Meth. 252: 57-62.
11. Patel et al., 1993, J. Immunol. Meth., 163:241-251.

12. Van Vlasselaer U.S. Pat. No. 5,648,223
13. Van Vlasselaer U.S. Pat. No. 5,474,687
14. Van Vlasselaer U.S. Pat. No. 5,646,004
15. Van Vlasselaer U.S. Pat. No. 5,840,502
16. Coulter et al. U.S. Pat. No. 5,576,185
17. StemCell Technologies, 1999/2000 Catalogue supplement

I claim:

1. A method for separating a first population of cells from a second population of cells in a sample comprising:
    linking dense particles to the first population of cells in the sample;
    layering the sample over a density separation medium (DSM) having a density at least about 0.001 g/cm$^3$ greater than the mean density of the second population of cells;
    allowing the cells to settle,
wherein the particle-linked first population of cells having a density that is greater than the density of the DSM settles to below the interface between the DSM and the sample and the second population of cells settles to the interface between the DSM and the sample; and
    recovering the second population of cells from the interface between the DSM and the sample, and/or recovering the first population of cells from below the interface between the DSM and the sample.

2. The method according to claim 1, comprising recovering the second population of cells from the interference between the DSM and the sample.

3. The method according to claim 2, wherein the second population of cells is selected from the group consisting of T cells, B cells, basophils, Natural Killer (NK) cells, dendritic cells, monocytes, macrophages, megakaryocytes, platelets, eosinophils, neutrophils, hematopoletic stems cells, mesenchymal stem cells, endothelial cells, epithelial cells, fibroblasts and tumour cells.

4. The method according to claim 1, comprising recovering the first population of cells from below the interface between the DSM and the sample.

5. The method according to claim 4, comprising removing the dense particles from the first population of cells.

6. The method according to claim 4, wherein the first population of cells is selected from the group consisting of T cells, B cells, basophils, NK cells, dendritic cells, monocytes, macrophages, megakaryocytes, platelets, eosinophils, neutrophils, hematopoietic stem cells, mesenchymal stem cells, endothelial cells, epithelial cells, fibroblasts and tumour cells.

7. The method according to claim 1, wherein the settling is accelerated by centrifugation.

8. The method according to claim 1, wherein the dense particles are selected from the group consisting of red blood cells, silica particles, metal particles, metal oxide particles, polymer particles and glass particles.

9. The method according to claim 8, wherein the dense particles are selected from the group consisting of red blood cells and silica particles.

10. The method according to claim 1, wherein the osmolarity of the DSM is approximately the same as the osmolarity of the sample.

11. The method according to claim 1, wherein the osmolarity of the DSM is about 270 to about 300 mOsm.

12. The method according to claim 1, wherein the first population of cells are linked to the dense particles by drug-drug receptor, antibody-antigen, hormone-hormone receptor, growth factor-growth factor receptor, carbohydrate-lectin, nucleic acid sequence-complementary nucleic acid sequence, enzyme-cofactor or enzyme-inhibitor binding.

13. The method according to claim 1, wherein the first population of cells have specific surface proteins and the dense particles are linked to these cells by antibodies specific for the cell surface proteins.

14. The method according to claim 1, wherein the density separation medium (DSM) has a density at least about 0.002 g/cm$^3$ greater than the mean density of the second population of cells.

15. The method according to claim 1, wherein the density separation medium (DSM) has a density at least about 0.004 g/cm$^3$ greater than the mean density of the second population of cells.

* * * * *